United States Patent
Shankar et al.

(10) Patent No.: US 9,353,246 B2
(45) Date of Patent: May 31, 2016

(54) PHOSPHOROUS-CONTAINING ALUMINUM CARBOXYLATE SALT FLAME RETARDANTS

(71) Applicant: Dow Global Technologies LLC, Midland, MI (US)

(72) Inventors: Ravi B. Shankar, Midland, MI (US); Matthew M. Yonkey, Sanford, MI (US); Shana P. Bunker, Midland, MI (US); Ted A. Morgan, Midland, MI (US)

(73) Assignee: Dow Global Technologies LLC

(*) Notice: Subject to any disclaimer, the term of this patent is extended or adjusted under 35 U.S.C. 154(b) by 0 days.

(21) Appl. No.: 14/428,041

(22) PCT Filed: Oct. 8, 2013

(86) PCT No.: PCT/US2013/063768
§ 371 (c)(1),
(2) Date: Mar. 13, 2015

(87) PCT Pub. No.: WO2014/062411
PCT Pub. Date: Apr. 24, 2014

(65) Prior Publication Data
US 2015/0225546 A1    Aug. 13, 2015

Related U.S. Application Data

(60) Provisional application No. 61/715,333, filed on Oct. 18, 2012.

(51) Int. Cl.
*C08K 5/5333* (2006.01)
*C07F 9/6571* (2006.01)
*C07F 9/40* (2006.01)
*C08K 5/00* (2006.01)
*C09K 21/12* (2006.01)
*C08K 5/5317* (2006.01)
*C08K 5/5357* (2006.01)
*C08J 9/00* (2006.01)

(52) U.S. Cl.
CPC ............... *C08K 5/5333* (2013.01); *C07F 9/40* (2013.01); *C07F 9/4006* (2013.01); *C07F 9/657181* (2013.01); *C08J 9/0038* (2013.01); *C08K 5/0066* (2013.01); *C08K 5/5317* (2013.01); *C08K 5/5357* (2013.01); *C09K 21/12* (2013.01); *C08J 2333/12* (2013.01); *Y10T 428/2982* (2015.01)

(58) Field of Classification Search
CPC ....... C08K 5/5333; C07F 9/40; C07F 9/4003; C07F 9/4006; C07F 9/4062; C07F 9/4065
USPC ...................... 556/14, 19; 524/115
See application file for complete search history.

(56) References Cited

U.S. PATENT DOCUMENTS

| 5,463,092 | A | * | 10/1995 | Hostetler | ............... | A61K 9/127 554/40 |
| 6,265,533 | B1 | * | 7/2001 | Regel | ................. | C08G 63/6926 264/211.21 |
| 6,365,071 | B1 | * | 4/2002 | Jenewein | ............. | C08K 5/3445 252/601 |
| 7,939,588 | B2 | | 5/2011 | Hong et al. | | |
| 2007/0149659 | A1 | | 6/2007 | Teixeira Pires et al. | | |

FOREIGN PATENT DOCUMENTS

| DE | 272092 | 9/1989 |
| GB | 2322373 | 8/1998 |
| WO | 2011163207 | 12/2011 |

OTHER PUBLICATIONS

Dziemidowicz, J.; Witt, D.; Sliwka-Kaszynska, J. R. Potassium Trimethylsilanolate-Mediated Conversion of Dialkyl Phosphonates to their Anhydrous Potassium Monoalkyl Phosphonates under mild, Non-aqueous conditions. Synthesis, 2005, pp. 0569-0574.*

Olagnon-Borgeot, S.; Chastrette, F. 31P NMR—Structure Correlations for Phosphocarboxylic Acids and Esters. Magnetic Resonance in Chemistry, vol. 33, pp. 971-976. 1995.*

Joanna Dziemidowicz et al: "Potassium Trimethylsilanolate-Mediated Conversion of Dialkyl Phosphonates to Their Anhydrous Potassium Monoalkyl Phosphonates Under Mild, Non-Aqueous Conditions", Synthesis, vol. 2005, No. 04, Feb. 9, 2005, pp. 569-574.

* cited by examiner

Primary Examiner — Mike M Dollinger
Assistant Examiner — Christina Wales
(74) Attorney, Agent, or Firm — Steven W. Mork

(57) ABSTRACT

Aluminum carboxylate salt having a formula of $Al[OCO(CH_2)_nP(O)(OR_1)(OR_2)]_3$ where $R_1$ and $R_2$ are hydrocarbyl groups that can optionally be joined and n is independently an integer between one and four is useful for forming an article of manufacture comprising a polymer compounded together the aluminum carboxylate salt to form a flame retardant polymer article.

11 Claims, No Drawings

PHOSPHOROUS-CONTAINING ALUMINUM CARBOXYLATE SALT FLAME RETARDANTS

BACKGROUND OF THE INVENTION

1. Field of the Invention

The present invention relates to phosphorous-containing aluminum carboxylate salt flame retardants for use in polymer articles of manufacture and polymer articles of manufacture comprising such flame retardants compounded with a polymer.

2. Introduction

Halogenated flame retardants are well known and well established in the industry for imparting flame retardant properties to polymer materials. However, there is a desire to move away from halogenated materials and identify non-halogenated flame retardants that are suitable for use in compounding with polymer resins. Popular non-halogenated flame retardants for use in compounding with polymer resins are phosphorous-containing flame retardants.

Some applications for polymer articles require use of a flame retardant that is not only a non-halogen flame retardant, but that is insoluble in the polymer. Phosphorous components such as triphenyl phosphate tend to be soluble in polymer resins. When the phosphorous containing flame retardant is soluble in the polymer resin with which it is compounded, the flame retardant lowers the softening temperature of the polymer resin, that is, it plasticizes the polymer resin. A polymer compounded with a plasticizer generally has a lower thermal dimensional stability, which means it is limited for use to applications at lower temperatures than a similar non-plasticized polymer. Therefore, it is desirable to not only identify a non-halogenated flame retardant suitable for use in compounding with a polymer, but one that is not soluble in the polymer.

A number of options are available for phosphorous-containing non-halogenated flame retardant additives that are insoluble in polymer resin.

WO2011/163207A2 discloses a method for making aluminum methyl methyl phosphonate (AMMP) in particulate form for use as a flame retardant additive.

US2007/0149659A1 discloses a salt of a phosphinic acid having particle sizes of 0.5-10 microns for use as a flame retardant in methacrylic compositions.

It would advance the art to identify an alternative insoluble non-halogenated flame retardant that is suitable for use in increasing flame retardant properties of polymer resin. It would be a particularly desirable advancement if the alternative insoluble non-halogenated flame retardant was a more effective flame retardant than AMMP and/or phosphinic acid salts.

BRIEF SUMMARY OF THE INVENTION

The present invention provides a novel non-halogenated flame retardant that is insoluble in polymer resins yet imparts flame retardant properties to the polymer resins. The present invention is the result of surprisingly discovering a novel phosphorous-containing aluminum carboxylate salt that efficiently imparts flame retardant properties to polymer resins without dissolving in the polymer resin and thereby plasticizing the polymer resin. Moreover, the phosphorous-containing aluminum carboxylate salt is a more effective flame retardant than aluminum methyl methylphosphonate (AMMP) and/or phosphinic acid salts.

In a first aspect, the present invention is an aluminum carboxylate salt having the following formula: $Al[OCO(CH_2)_nP(O)(OR_1)(OR_2)]_3$ where $R_1$ and $R_2$ are hydrocarbyl groups that can optionally be joined and n is independently an integer between one and four.

In a second aspect, the present invention is an article of manufacture comprising a polymer compounded together with the aluminum carboxylate salt of the first aspect.

Desirably, the article of manufacture ("polymer article") is the form of polymeric foam.

The present invention is useful as a flame retardant for polymers.

DETAILED DESCRIPTION OF THE INVENTION

Test methods refer to the most recent test method as of the priority date of this document when a date is not indicated with the test method number. References to test methods contain both a reference to the testing society and the test method number. The following test method abbreviations and identifiers apply herein: ASTM refers to ASTM International (formerly American Society for Testing and Materials); EN refers to European Norm; DIN refers to Deutsches Institut für Normung; and ISO refers to International Organization for Standards.

"Multiple" means two or more. "And/or" means "and, or as an alternative". All ranges include endpoints unless otherwise indicated.

"Polymer", unless indicated otherwise, refers to both homopolymer and copolymer. Unless otherwise indicated, "copolymer" includes block copolymer, graft copolymer, alternating copolymer and random copolymer.

"(meth)acrylic" refers to both "methacrylic" and "acrylic". Hence, a "(meth)acrylic" polymer is a polymer selected from methacrylic polymers and acrylic polymers. "Methacrylic" polymers contain polymerized methacrylic monomers. "Acrylic" polymers contain polymerized acrylic monomers. A "(meth)acrylic" polymer can be a copolymer containing both methacrylic monomers and acrylic monomers and as such can be both a methacrylic polymer and an acrylic polymer. If a copolymer is "(meth)acrylic-free" that means the copolymer lacks both methacrylic and acrylic monomer units copolymerized therein.

The present invention is an aluminum carboxylate salt having the following formula: $Al[OCO(CH_2)_nP(O)(OR_1)(OR_2)]_3$, which corresponds to the following structure:

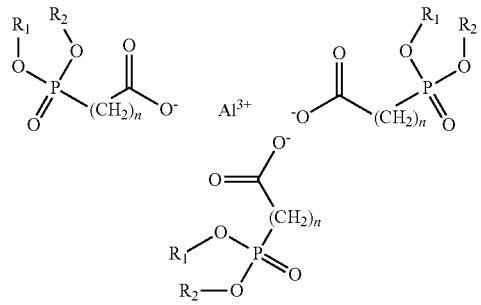

where $R_1$ and $R_2$ are hydrocarbyl groups and n is independently an integer between one and four, preferably between one and three and more preferably selected from one and two. The $R_1$ and $R_2$ groups are independently selected for each occurrence.

Desirably, any combination of one $R_1$ and one $R_2$ group has six carbons or less, preferably five carbons or less and even more preferably four carbons or less and at the same time generally has two carbons or more, preferably three carbons or more and still more preferably four carbon or more. The $R_1$ and $R_2$ hydrocarbyl groups are desirably independently selected from ethyl and methyl groups. The $R_1$ and $R_2$ hydrocarbyl groups can, optionally be joined to form a ring structure with the two oxygen atoms and phosphorous. One desirable option for a combination of $R_1$ and $R_2$ associated with the same phosphorous atom and where $R_1$ and $R_2$ are joined to form a ring structure is the following structure:

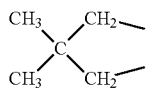

"Independently selected" means that each occurrence of the variable can be selected from the specified options regardless of what other occurrences of the variable are and regardless of what other variables are. For example, one occurrence of $R_1$ can be ethyl while another can be methyl. It is desirable for each occurrence of $R_1$ to be the same and each occurrence of $R_2$ to be the same, though $R_1$ does not need to be the same as $R_2$. More desirably, each occurrence of $R_1$ and $R_2$ are the same. It is desirable for n to be the same value in each occurrence.

Notably, while the most preferred form of the aluminum carboxylate salt has three $[OCO(CH_2)_nP(O)(OR_1)(OR_2)]$ groups associated with each aluminum (III) atom, it is conceivable and acceptable for fewer than all of the counter ions of the aluminum (III) to be $[OCO(CH_2)_nP(O)(OR_1)(OR_2)]$ groups. It is to be understood that a designation of $[OCO(CH_2)_nP(O)(OR_1)(OR_2)]_3$ includes formulas of $[OCO(CH_2)_nP(O)(OR_1)(OR_2)]_x$ where x is 2.5 or higher, preferably 2.7 or higher, yet more preferably 2.9 or higher and most desirably is 3.0. In each of these cases, the value of "x" rounds to 3.

Desirably, the aluminum carboxylate salt is selected from a group consisting of aluminum tris(2-(diethoxyphosphoryl)acetate), aluminum tris(2-(5,5-dimethyl-2-oxido-1,3,2-dioxaphosphinan-2yl)acetate), aluminum tris(2-dimethoxyphosphoryl)acetate, and aluminum tris(3-(diethoxyphosphoryl)propanoate).

Aluminum tris(2-(diethoxyphosphoryl)acetate) corresponds to an aluminum carboxylate salt where each occurrence of R is an ethyl and each occurrence of n is 1 so as to have the following formula: $Al[OCO(CH_2)_1P(O)(OC_2H_5)_2]_3$, and which has the following structure:

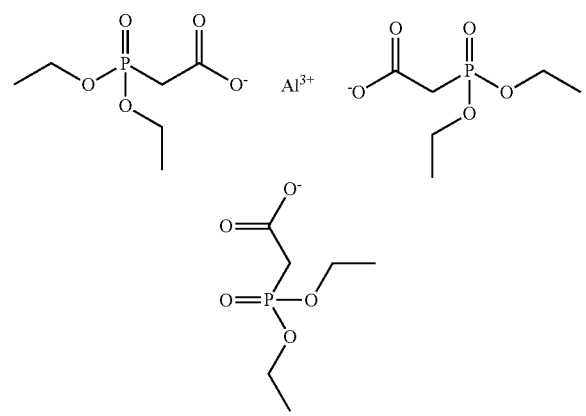

Aluminum tris(2-(5,5-dimethyl-2-oxido-1,3,2-dioxaphosphinan-2yl)acetate) is an example of an aluminum carboxylate salt where R1 and R2 are joined to form a ring structure having the following structure:

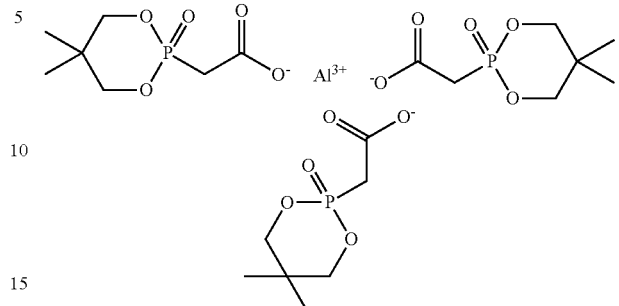

Aluminum tris(2-dimethoxyphosphoryl)acetate has the following structure:

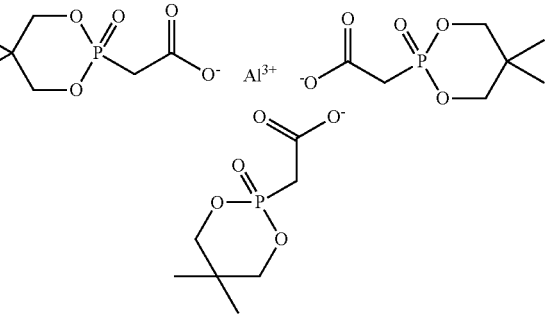

Aluminum tris(3-(diethoxyphosphoryl)propanoate) has the following structure:

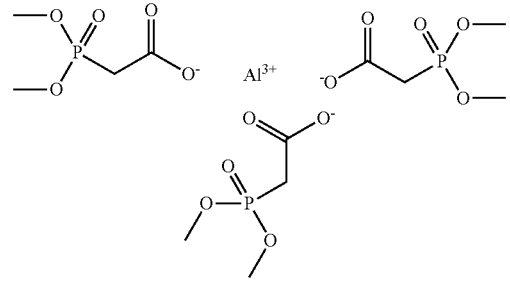

A preferred method for preparing the aluminum carboxylate salt of the present invention is by heating a mixture of a phosphorous-containing carboxylic acid (3 mole parts) with aluminum hydroxide (one mole part) in water for eight hours and then concentrating the reaction mixture under reduced pressure to provide crude product. Purify the crude product by washing with acetone and drying under vacuum.

The aluminum carboxylate salt of the present invention is a solid at the processing temperature of many polymers and at the use temperature of many polymers. As a result, the aluminum carboxylate salt does not plasticize the polymer in which it is compounded. However, the aluminum carboxylate salt should be compounded with a polymer so that the salt is well dispersed in the polymer in order to most effectively impart flame retardant properties to the resulting polymer compounded with the aluminum carboxylate salt (that is, the article of manufacture, or "polymer article"). Therefore, it is advantageous for the aluminum carboxylate salt to be in particulate form when compounding with a polymer and when dispersed within a polymer to form a polymer article. In particular, it is desirable for the aluminum carboxylate salt to have an average particle size of ten micrometers or less so that it can be well dispersed throughout a polymer. Determine particle size of the aluminum carboxylate salt by light scattering analysis using a Beckman Coulter laser diffraction particle size analyzer and following the method for that device. Smaller particle sizes are desirable for the flame retardant in order to achieve distribution of the flame retardant throughout as much of a polymer as possible rather than having the flame retardant localized in concentrated spots in the polymer article.

The aluminum carboxylate salt of the present invention is a component in the polymer article of the present invention. Desirably, the polymer article comprises sufficient aluminum carboxylate salt so provide two weight-percent (wt %) or more, preferably 2.5 wt % or more, still more preferably 3 wt % or more and possibly 3.5 wt % or more while at the same time typically less than 5 wt %, preferably 4 wt % or less phosphorous based on polymer article weight (for avoidance of doubt, "polymer article weight" refers to the weight of polymer in the article in addition to the weight of any components dispersed within the polymer, but does not include the weight of components that may be adhered to a surface of the polymer such as a facer adhered to a surface of a polymeric foam). Determine the concentration of phosphorous in a polymer article using $^{13}C$ or $^{31}P$ nuclear magnetic resonance spectroscopy.

The polymer article of the present invention contains polymer resin, the aluminum carboxylate salt and optional additives. The polymer in the polymer article can comprise thermoplastic and/or thermoset polymers. Desirably, more than 50 wt %, preferably 75 wt % or more, still more preferably 90 wt % or more, yet more preferably 95 wt % or more and possibly 100 wt % of all polymers in the polymer article are thermoplastic polymers. Examples of suitable thermoplastic polymers include styrenic polymers and (meth)acrylic polymers.

Examples of suitable styrenic polymers include homopolymers of styrene and styrene derivatives as well as copolymers of different monomers wherein a majority of the monomers are selected from styrene and styrene derivatives. Specifically desirably styrenic polymers include polystyrene homopolymer, styrene-acrylonitrile copolymer, and polystyrene-co-ethyl acrylate (PS-co-PEA).

Examples of suitable (meth)acrylic polymers include polymethylmethacrylcate (PMMA), polymethylmethacrylate-co-ethylmethacrylate (PMMA-co-EMA) copolymers, polymethylmethacrylate-co-polyethyl acrylates (PMMA-co-PEA), and polymethyl methacrylate-co-polybutyl methacrylate (PMMA-co-PBMA).

Optional additional additives that can be in the polymer article include any one or combination of more than one of the following: additional flame retardant (such as brominated polymers), flame retardant synergists (such as aluminum oxide), antioxidant additives, nucleating agents (for example, talc, magnesium silicate and calcium carbonate), extrusion aids (for example, zinc stearate and barium stearate), infrared attenuating agents (for example, graphite, carbon black and titanium dioxide), pigments and colorants. The total amount of additional additives is desirably less than two wt % relative to total polymer article weight. The total amount of additional additives in the polymer article is generally 0.5 wt % or less based on total polymer article weight. The polymer article can also be free of any one or any combination of more than one of the aforementioned optional additional additives. For example, the polymer article can be free of flame retardant synergists, additional flame retardants beyond the aluminum carboxylate salt, or free of both flame retardant synergists and additional flame retardants.

One method for compounding the aluminum carboxylate salt into a polymer to form a polymer article is by melt blending in a batch mixing system such as a Haake Rheomix OS. Heat the batch mixer and add the polymer while the mixer is running at, for example, 60 revolutions per minute (RPM). Once the polymer melts, add the aluminum carboxylate salt and continue mixing at 60 RPM for approximately 10 minutes. Additional additives can also be compounded into the polymer article in a similar manner.

The polymer article can be in the form of polymeric foam wherein the polymer defines multiple cells dispersed within a continuous matrix of the polymer resin. The polymer article can be made into polymeric foam by any foaming method. For example, the polymer article can be subject to an extrusion foam process or an expanded foam process. As an example of an extrusion process, the polymer article can be added to an extruder (or actually formed by compounding the resin and aluminum carboxylate salt together in an extruder), melt blended with a blowing agent under pressure and then extruded into an environment of lower pressure and allowed to expand into a polymeric foam. As an example of an expanded foam process, the polymer article can be compounded with a blowing agent and extruded into pellets. The pellets can then be combined in a mold and heated sufficiently to soften the polymer resin in the polymer article allowing the blowing agent to expand the pellets to fill the mold space and fuse with neighboring expanded pellets. The aluminum carboxylate salt can serve as a flame retardant in the resulting polymeric foam.

The following examples and comparative examples further illustrate embodiments of the present invention.

EXAMPLES

Example 1

Aluminum Tris(2-(diethoxyphosphoryl)acetate)

Use as a reaction vessel a 1000 milliliter (mL) three neck round bottom flack fitted with a mechanical stirrer, glass stopper and a condenser with a nitrogen inlet. Charge the vessel with diethyl phosphonoacetic acid (50 mL) followed by addition of water (400 mL) and aluminum hydroxide monohydrate (9.21 grams). Heat the resulting solution to reflux and hold at that temperature for eight hours. Remove the water using a rotovap to leave behind a solid material. Add 200 mL of acetone and isolate the solid by vacuum filtration using a Buchner funnel and wash with additional water and acetone (three times with 200 mL of each) to clean the solid product. Transfer the solid product to a glass bottle and place in a vacuum oven to dry overnight. The yield of solid product is 46 grams. The solid product (Example 1) is an aluminum carboxylate salt of the present invention having the formula: $Al[OCO(CH_2)_1P(O)(OC_2H_5)_2]_3$.

Mill the solid product to achieve particulates by grinding and homogenizing 20 grams of the solid in a tungsten carbide contain for 20 minutes using a Spex 8510 Shatterbox (a ball mill). The resulting solid product has an average particle size of less than ten micrometers as determined by laser light scattering as describe above.

Example 2

Aluminum tris(2-(5,5-dimethyl-2-oxido-1,3,2-dioxaphosphinan-2yl)acetate)

Prepare a reaction vessel using a 250 mL single neck round bottom flask by fitting it with a short path distillation head with nitrogen inlet. Charge the vessel with 50.02 grams (g) benzyl bromoacetate and 51.27 g 2-isopropoxy-5,5-dimethyl-1,3,2-dioxaphosphinane. Heat the solution very slowly to 140° C. and hold for two hours. Purify the resulting solution by chromatography on a silica gel column using hexane/ethyl acetate (40/60) as eluent. Condense appropriate fractions to afford product as a clear viscous oil. The yield of the resulting benzyl2-(5,5-dimethyl-2-oxido-1,3,2-dioxaphosphinan-2-yl)acetate is 42.11 g.

Prepare a reaction vessel from a 250 mL Hastelloy-C Parr reactor by fitting with a mechanical stirrer, a pressure monitor and a gas inlet. Charge the vessel with 21.05 g benzyl2-(5,5-dimethyl-2-oxido-1,3,2-dioxaphosphinan-2-yl)acetate, 70 mL methanol containing 15% formic acid and 0.4 g of 10% palladium on carbon catalyst. Stir the reactor and charge the vessel with hydrogen to 2.1 mega Pascals (300 pounds per square inch). Allow the reactor to stir approximately 14 hours. Release the pressure and filter the solution and concentrate the filtrate under reduced pressure to yield a white solid. Transfer the solid product to a glass bottle and place in a vacuum oven to dry overnight. The yield of the resulting 2-(5,5-dimethyl-2-oxido-1,3,2-dioxaphosphinan-2-yl)acetic acid is 14.0 g.

Prepare a reaction vessel from a 1000 mL single neck round bottom flask by fitting with a condenser with a nitrogen inlet. Charge the vessel with 31.55 g 2-(5,5-dimethyl-2-oxido-1,3,2-dioxaphosphinan-2-yl)acetic acid followed by 100 mL water and 4.38 g aluminum hydroxide monohydrate. Heat the resulting solution to 90° C. and hold at that temperature for 24 hours. Isolate the solid by vacuum filtration using a fritted funnel and wash with 400 mL acetone. Transfer the solid product to a glass bottle and place in a vacuum oven to dry overnight. The yield of the solid product of Aluminum tris(2-(5,5-dimethyl-2-oxido-1,3,2-dioxaphosphinan-2yl) acetate) is 31.25 g.

Example 3

Aluminum tris(2-dimethoxyphosphorvl)acetate

Use as a reaction vessel a 1000 milliliter (mL) single neck round bottomed flask fitted with a condenser with a nitrogen inlet. Charge the vessel with dimethylphosphonoacetic acid (46.65 g) followed by the addition of water (200 mL) and aluminum hydroxide monohydrate (9.18 g). Heat the resulting solution to 90° C. and hold at that temperature for nine hours. Remove the water using a rotovap to leave behind a solid material. Add 500 mL of acetone and isolate the solid by vacuum filtration using a Buchner funnel and wash with acetone (400 mL). Transfer the solid product to a glass bottle and place in a vacuum oven to dry overnight. The yield of the solid product, aluminum tris(2-dimethoxyphosphoryl)acetate, is 45.67 g.

Example 4

Aluminum tris(3-(diethoxyphosphoryl)propanoate)

Use as a reaction vessel a 250 milliliter (mL) one neck round bottom flack fitted with a magnetic stir bar and a condenser with a nitrogen inlet. Charge the vessel with ethyl 3-(diethoxyphosphoryl)propanoate (25.0 g, 0.10 mol) in tetrahydrofuran (THF) (60 mL) followed by a solution of sodium hydroxide (4.62 g, 0.11 mol) in 10 mL of water and stir the mixture overnight. Acidify the reaction mixture with Concentrated HCl till pH 2. Separate the THF layers formed and concentrate the aqueous layer to a white solid. Transfer the solid product to a glass bottle and place in a vacuum oven to dry overnight. The yield of solid product, 3-(diethoxyphosphoryl)propanoic acid, is 21.2 grams (90%).

Use as a reaction vessel a 500 milliliter (mL) single neck round bottomed flask fitted with a condenser with a nitrogen inlet. Charge the vessel with 3-(diethyoxyphosphoryl)propanoic acid (20.30 g) followed by the addition of water (150 mL) and aluminum hydroxide monohydrate (2.709 g). Heat the resulting solution to 90° C. and hold at that temperature for eight hours. Remove the water using a rotovap to leave behind a solid material. Add 100 mL of acetone and isolate the solid by vacuum filtration using a Buchner funnel and wash with acetone (100 mL). Transfer the solid product to a glass bottle and place in a vacuum oven to dry overnight. The yield of the solid product, aluminum tris(3-(diethoxyphosphoryl)propanoate), is 12.45 g.

Large Scale Compounding

Example 1-1

Prepare a polymer article by compounding Example 1 with a polymethylmethacrylate-co-polyethylacrylate copolymer (8.9 wt % ethyl acrylate and Tg of 95.3° C., melt flow rate of 10 dg/min per ASTM D1238 (3.8 kg/23° C.); for example VM100 from Arkema) using a Haake RhoMix OS.

Prepare a batch of compound by first heating the bowl of the instrument to 180 degrees Celsius (° C.) and then adding 46.9 grams (g) of PMMA-co-PEA copolymer to the instrument bowl while mixing at 60 revolutions per minute and allowing the copolymer to melt. Add to the molten polymer 11.5 g of Example 1 that has been milled as described above. Mix the materials together for 10 minutes at 60 revolutions per minute while maintaining a temperature of 180° C. using pneumatic cooling. The resulting polymer article (Example 2) is pressed into plaques at 180° C. under a pressure of 173 megaPascals for 10 minutes to produce plaques 101 millimeters (mm) by 101 mm by 1.5 mm in size for characterization.

Determine the limiting oxygen index (LOI) for Example 2 according to ASTM test procedure D2863 with a modification that test samples are molded plaques of Example 2 cut to dimensions of 100 millimeters (mm) by 6.5 mm by 1.5 mm. Results are in Table 1.

Determine 5% weight loss temperature and non-organic residues using thermogravimetric analysis (TGA) using a Q500 TGA (from TA Instruments) with an auto sampler tray. Characterize 20-40 milligram test samples of Example 2 by measuring the amount of material out in an aluminum pan and placing the material in a platinum pan. Use nitrogen at a flow rate of 40 mL per minute as a balance purge gas and compressed air at 60 mL per minute flow for the sample purge gas. Increase the temperature from ambient (23° C.) to 500° C. at a rate of 5° C. per minute. Use the TA Universal Analysis 2000 software to analyze the weight loss versus temperature and to quantify non-organic residues. Results are in Table 1.

Determine glass transition temperature for the polymer article according the ASTM method E1356-03. Results are in Table 1.

Comparative Examples A and B

Prepare Comparative Examples A and B in like manner as Example 1-1 except with the following changes:
Comparative Example (Comp Ex) A: Use 50 grams of PMMA-co-PEA and no flame retardant additive.
Comp Ex B: Use 51 g PMMA-co-PEA and instead of using Example 1 as a flame retardant use 6 g triphenyl phosphate.
Characterize the resulting polymer articles in like manner as Example 1-1. Results are in Table 1.

TABLE 1

|  | Example 1-1 | Comp Ex A | Comp Ex C |
| --- | --- | --- | --- |
| Component |  |  |  |
| PMMA-co-PEA(wt %) | 80.3 | 100 | 89.5 |
| Ex 1 FR (wt %) | 19.7 | 0 | 0 |
| AMMP FR (wt %) | 0 | 0 | 0 |
| Triphenyl Phosphate FR (wt %) | 0 | 0 | 10.5 |
| Characterization |  |  |  |
| Wt % phosphorous in Composition | 3 | 0 | 1 |
| LOI | 25.5 | 17 | 20.5 |
| Glass Transition Temp (° C.) | 100 | 96 | 75.3 |
| TGA wt % residual | 9.1 | 0 | 0 |

The data in Table 1 reveals the following:
1. The aluminum carboxylate salt of the present invention imparts greater flame retardant properties than triphenyl phosphate. This is evident from the LOI values, which show that the aluminum carboxylate salt of the present invention provides a higher LOI than triphenyl phosphate at similar phosphorous loadings.
2. The aluminum carboxylate salt of the present invention does not plasticize the polymer article while triphenyl phosphate flame retardants do. This is evident by comparing the glass transition temperature (Tg) of the composition containing flame retardant to that of Comp Ex A, which does not contain any flame retardant. A decrease in Tg indicates plasticization is occurring. The aluminum carboxylate salt example (Example 2) actually demonstrates an increase in Tg.
3. The sample containing aluminum carboxylate salt induces more charring in a thermal gravimetric analysis than the comparative examples, which is indicative that the aluminum carboxylate salt will induce more charring under flame conditions as well.

Similar results are expected for any of the aluminum carboxylate salts within the scope of the present invention.

Small Scale Compounding

Prepare small scale compounding samples by melt blending PMMA-co-PEA as described for Example 1-1 with a flame retardant using a Batch SFEM (small-scale extensional mixer) from Randcastle Extrusion Systems, Inc. The mixer has a rotary mixing element such as the one described in patent U.S. Pat. No. 6,962,431 that is driven by a motor inside a cylindrical cavity. The rotor diameter is 25 millimeters with a length-to-diameter ratio (L/D) equal to four. Clearances between the rotor and the cavity are one millimeter. The cavity is equipped with a die gate to allow sample retrieval. The PMMA-co-PEA is premixed with the flame retardant and then added to the feed port of the mixer and pushed in the mixer with a feeding ram over approximately one minute. Processing is at 180° C. for 10 minutes at a rotor speed of 100 revolutions per minute. After mixing, stop the rotor and open the die gates. Restart the rotor to induce extrusion of a molten strand of 5 to 6 cubic centimeters.

Notably, the small scale mixer has regions of compression and regions of elongation/extension. It is possible that the small scale mixing equipment is agglomerating flame retardant particles during the "compression" portion of the mixing, which could reduce the flame retardant properties of the resulting compound (lower LOI values than achievable with larger scale compounding).

Example 1-2

Prepare a polymer article by small scale compounding using Example 1 as the flame retardant.

Example 2-1

Prepare a polymer article by small scale compounding using Example 2 as the flame retardant.

Example 3-1

Prepare a polymer article by small scale compounding using Example 3 as the flame retardant.

Example 4-1

Prepare a polymer article by small scale compounding using Example 4 as the flame retardant.

Comparative Example B

Prepare a polymer article by small scale compounding using an AMMP flame retardant. Prepare the AMMP flame retardant as follows: charge a 500 milliliter (mL) three necked round bottom flask with a mechanical stirrer and condenser with attached nitrogen inlet with aluminum hydroxide hydrate (9.61 g, 0.1 moles). Then add dimethyl methyl phosphonate (101.25 g, 0.82 moles) to form a milky white heterogeneous solution. Add a tetra-n-butylphosphonium bromide (0.234 g) and heat the mixture to 165° C. and hold at that temperature for 9 hours. Cool the mixture and allow to stir at room temperature 8 more hours to produce a thick white colored milky heterogeneous mixture. Transfer the reaction mixture to a 1000 mL single necked round bottom flask using methanol as the transfer solvent. Remove the solvent and some of the excess dimethyl methylphosphonate using a rotary evaporator heated to 95° C. Add approximately 200 mL of methanol to the flask and collect the solid by vacuum filtration on a Buchner funnel. Wash the isolated solid multiple times with additional methanol to remove any residual dimethyl methylphosphonate. Place the resulting white solid into a glass bottle and place in a vacuum oven heated to 70° C. overnight. The final product (AMMP) is a white solid having a 5% weight loss temperature of 313° C. as determined by thermogravimetric analysis.

Comparative Example C

Prepare a polymer article by small scale compounding using triphenyl phosphate as the flame retardant.
Table 2 presents a summary of the small scale compounding samples and results.

TABLE 2

|  | Ex 1-2 | Ex 2-1 | Ex 3-1 | Ex 4-1 | Comp Ex B | Comp Ex C |
|---|---|---|---|---|---|---|
| Component |  |  |  |  |  |  |
| PMMA-co-PEA(wt %) | 80.3 | 79 | 83 | 80 | 88.5 | 89.5 |
| Ex 1 FR (wt %) | 19.7 |  |  |  |  |  |
| Ex 2 FR (wt %) |  | 21 |  |  |  |  |
| Ex 3 FR (wt %) |  |  | 17 |  |  |  |
| Ex 4 FR (wt %) |  |  |  | 20 |  |  |
| AMMP FR (wt %) |  |  |  |  | 11.5 |  |
| Triphenyl Phosphate FR (wt %) |  |  |  |  |  | 10.5 |
| Characterization |  |  |  |  |  |  |
| Wt % phosphorous in Composition | 3 | 3 | 3 | 3 | 3 | 1 |
| LOI | 22 | 21.5 | 20 | 22.5 | 21 | 20.5 |
| Glass Transition Temp (° C.) | 95 | 92 | 99 | 100 | 96 | 78.3 |
| TGA wt % residual | 6.5 | 4.8 | 9.8 | 13.2 | 5.7 | 0 |

The data in Table 2 indicates that the inventive flame retardants provide LOI performance without extensive plasticizing the polymer even in small scale compounding that is equivalent or better than AMMP and triphenyl phosphate. Notably, triphenyl phosphate (Comp Ex C) demonstrates undesirable plasticization of the polymer, as is evident by the lower glass transition temperature, even at a one wt % phosphorous loading.

What is claimed is:

1. An aluminum carboxylate salt having the following formula: $Al[OCO(CH_2)_nP(O)(OR_1)(OR_2)]_3$ where $R_1$ and $R_2$ are hydrocarbyl groups that can optionally be joined and n is independently an integer between one and four.

2. The aluminum carboxylate salt of claim 1, where $R_1$ and $R_2$ are independently selected from ethyl groups, methyl groups and ring structures where $R_1$ and $R_2$ are joined.

3. The aluminum carboxylate salt of claim 1, where n is selected from one and two.

4. The aluminum carboxylate salt of claim 1, wherein n is one in each occurrence and $R_1$ and $R_2$ are ethyl groups in each occurrence.

5. The aluminum carboxylate salt of claim 1, further characterized as being in particulate form with an average particle size of ten micrometers or less as determined by light scattering.

6. An article of manufacture comprising a polymer compounded together with the aluminum carboxylate salt of any of the previous claims.

7. The article of manufacture of claim 6, further characterized by comprising sufficient aluminum carboxylate salt so to contain at least three weight-percent phosphorous based on polymer article weight.

8. The article of manufacture of claim 6, further characterized by the polymer comprising polymers selected from styrenic and (meth)acrylic polymers.

9. The article of manufacture of claim 6, further characterized by the polymer defining multiple cells therein so that the article of manufacture is in the form of polymeric foam.

10. The article of manufacture of claim 6, further characterized by being free of flame retardant synergists.

11. The article of manufacture of claim 6, further characterized by the concentration of phosphorous in the article of manufacture being less than five weight-percent based on total polymer article weight.

* * * * *